| (12) | United States Patent | (10) Patent No.: | US 6,242,483 B1 |
|---|---|---|---|
| | McLaughlin et al. | (45) Date of Patent: | Jun. 5, 2001 |

(54) SELECTIVELY CYTOTOXIC ACETOGENIN COMPOUNDS

(75) Inventors: Jerry L. McLaughlin, West Lafayette, IN (US); David Craig Hopp, Omaha, NE (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/423,139

(22) PCT Filed: May 5, 1998

(86) PCT No.: PCT/US98/08989

§ 371 Date: Dec. 15, 1999

§ 102(e) Date: Dec. 15, 1999

(87) PCT Pub. No.: WO98/49895

PCT Pub. Date: Nov. 12, 1998

Related U.S. Application Data

(60) Provisional application No. 60/045,819, filed on May 5, 1997.

(51) Int. Cl.⁷ .................................................... A01N 43/08
(52) U.S. Cl. ............................................ 514/473; 549/320
(58) Field of Search ............................. 514/473; 549/320

(56) References Cited

PUBLICATIONS

Chang et al, J. Nat. Prod., vol. 56, No. 10, pp. 1688–1694 (abstract), Oct. 1993.*
Alkofahi et al, Experientia, vol. 46, No. 5, pp. 539–541 (abstract), May 1990.*
Li et al, J. Nat. Prod., vol. 53, No. 1, pp. 81–67 (abstract), Jan. 1990.*
Alkofahi et al, Experientia, vol. 44, No. 1, pp. 83–85 (abstract), Jan. 1988.*
Wu et al, J. Nat. Prod., vol. 58, No. 6, pp. 830–836 (abstract), Jun. 1995.*
Wu et al, J. Nat. Prod., vol. 58, No. 6, pp. 908–915 (abstract), Jun. 1995.*
Zeng et al, J. Nat. Prod, vol. 59, No. 11, pp. 1035–1042, Nov. 1996.*

* cited by examiner

Primary Examiner—James H. Reamer
(74) Attorney, Agent, or Firm—Barnes & Thornburg

(57) ABSTRACT

The isolation of three new mono-tetrahydrofuran ring acetogenins from the bark of *Annona squamosa* is described. Each of these compounds bears a carbonyl group at the C-9 position and two hydroxyls that flank the tetrahydrofuran ring. These compounds exibit selective cytotoxic activity against certain specific human tumor cells.

4 Claims, No Drawings

SELECTIVELY CYTOTOXIC ACETOGENIN COMPOUNDS

CROSS-REFERENCES TO RELATED APPLICATIONS

This application is a U.S. national application of international application Ser. No. PCT/US98/08989 filed May 5, 1998, which claims priority to U.S. provisional application Ser. No. 60/045,819 filed May 5, 1997.

GOVERNMENT RIGHTS

This invention was made with United States Government support under Grant No. CA30909, awarded by the National Institute of Health. The United States Government has certain rights in the invention.

FIELD OF THE INVENTION

This invention relates to the isolation, identification, and use of natural products. More particularly this invention is directed to substantially pure forms of cytotoxic Annonaceous acetogenins and the use of those compounds in preparing chemotherapeutic compositions.

BACKGROUND AND SUMMARY OF THE INVENTION

Annonaceous acetogenins are a well established class of natural compounds that have been isolated from plants in the Annonaceae family. It has been reported that various members of this class of compounds exhibit significant bioactivities. Acetogenins are $C_{35}$–$C_{39}$ compounds that typically contain two long hydrocarbon chains, one of which connects a terminal 2,4-disubstituted-γ-lactone to a variable number of tetrahydrofuran (THF) rings. The hydrocarbon chains contain a number of oxygenated moieties which can be hydroxyls, acetoxyls and/or ketones. Recently, single-ring acetogenins containing double bonds, epoxide compounds which lack THF rings and a compound lacking both epoxides and THF rings have been reported. These interesting newer compounds support the proposed polyketide origin of the Annonaceous acetogenins and provide additional clues to their biogenesis.

All acetogenins found to date contain multiple stereocenters, the elucidation of which often presents daunting stereochemical problems. Because of their waxy nature, the acetogenins do not produce crystals suitable for X-ray crystallographic analysis. Relative stereochemistries of ring junctions have typically been determined by comparison of natural compounds with synthetic model compounds and such methods have proven to be invaluable with the acetogenins. Recently, the absolute stereochemistries of the carbinol centers of acetogenins have been determined with the help of synthetic model compounds and high field nuclear magnetic resonance (NMR) analysis of their methoxyfluoromethylphenylacetic acid (MPTA) esters (Mosher esters).

Most Annonaceous acetogenins are potently bioactive, but the mode of action of these compounds was unknown until Londerhausen et al. concluded in *Pesticide Science* 427–438 (1991), that they act to inhibit complex I of mitochondrial oxidative phosphorylation with an activity several times that of rotenone.

The present invention is directed to the isolation and characterization of the bioactivity of novel acetogenins. More particularly the present invention is directed to three new mono-tetrahydrofuran (THF) ring acetogenins each of which were isolated from the bark of *Annona squamosa*. These compounds each bear two hydroxyls that flank the THF ring and a carbonyl group at the C-9 position. The compounds were isolated using the brine shrimp lethality assay as a guide for the bioactivity-directed fractionation. It has been discovered that acetogenins possessing a hydroxyl flanking mono-THF system with a carbonyl in the aliphatic chain exhibit high selective cytotoxicity to various tumor cells and thus can be used to prepare chemotherapy compositions for administrations to patients having tumors.

DETAILED DESCRIPTION OF THE INVENTION

The present invention is directed to three novel acetogenins, mosinone A (1), mosin B (2) and mosin C (3). Each of those three compounds bears a single tetrahydrofuran (THF) ring and a carbonyl at the C-9 position. The specific stereochemistry of these three compounds is shown below, wherein "X", "Y" and "Z" designate the stereochemistry across the THF ring.

Mosinone A:

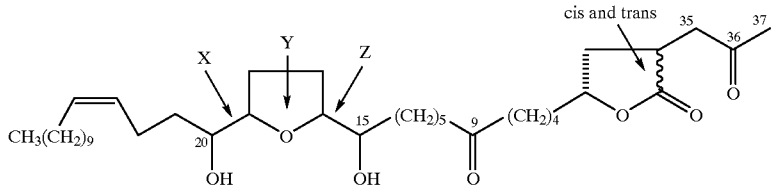

wherein X is threo, Y is trans, Z is threo and $C_{15}/C_{20}$ is R/R.

Mosin B and C:

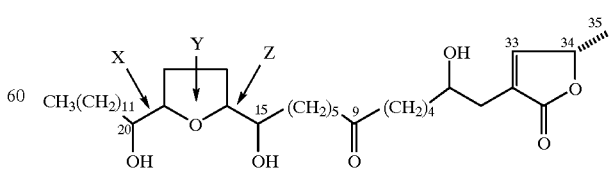

wherein, for mosin B: X is threo/erythro, Y is trans, Z is threo/erythro and $C_{15}/C_{20}$ is R/S or S/R; and for mosin C: X is threo, Y is cis, Z is threo and $C_{15}/C_{20}$ is R/S.

These three compounds and one previously known acetogenin, annoreticuin-9-one (4) were isolated from the bark of A. squamosa. The stereochemistry of annoreticuin-9-one is as follows:

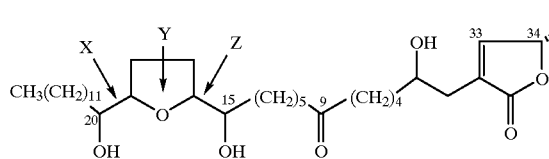

wherein X is threo, Y is trans, Z is threo and $C_{15}/C_{20}$ is R/R.

(2,4-cis and trans)-Mosinone A (1) is a mixture of keto-lactone compounds bearing a threo/trans/threo ring relationship and a double bond two methylene units away from the flanking hydroxyl. The other two new acetogenins differ in their stereochemistries around the THF ring; mosin B (2) has a threo/trans/erythro configuration across the ring and mosin C (3) possesses a threo/cis/threo relative stereochemistry. Annoreticuin-9-one (4), a known acetogenin which bears a threo/trans/threo ring configuration and a C-9 carbonyl and is new to this species. The structures were elucidated based on spectroscopic and chemical methods.

Each of these compounds was isolated from the bark of A. squamosa. Approximately 7.4 kg of dried bark was pulverized and extracted with ethanol then further partitioned to yield 545.5 g of F005 (BST $LC_{50}$=1.5155). From this, 500.5 g was loaded onto a silica gel (Si gel) column and eluted with hexane and increasing percentages of chloroform, then chloroform and increasing percentages of methanol. Sixty fractions were collected, and fractions 30–36 were combined (21.67 g). This material was separated on successive open columns packed with Si gel. Repeated HPLC of fractions active in the brine shrimp lethality test (BST) yielded compounds 1–4. The procedure for conducting the BST test is described in Meyer et al. *Planta Med.* 45, p. 31–34 (1982).

(2,4-cis- and trans)-Mosinone A (1) was isolated in a mixture as a white waxy solid. The molecular weight of 1 was shown to be 620, based on the $MH^+$ peak at 621 in the CIMS. The compound was established as having the elemental composition of $C_{37}H_{64}O_7$ by the high resolution CIMS peak for the $MH^+$ at m/z 621.4723 (621.4730 calcd.). Signals in the $^1H$ NMR of 1 at δ 4.39 and 4.55 (Table 1), with a combined integration for one proton, were assigned to H-4 and indicated the presence of a (2,4-cis and trans)-mixture at the ketolactone moiety which is common for acetogenins of this type. Resonances in the $^1H$ NMR of 1 at δ 2.65 and 3.07 (H-35) and at 2.20 (H-37) further substantiated this assignment. In the $^{13}C$ NMR of 1, signals at δ 205.5 (C-36), 178.7 and 178.1 (C-1), 44.2 and 43.7 (C-2), 79.0 and 78.5 (C-4), and 23.7 (Table 2) also confirmed that 1 is a cis/trans mixture of ketolactone isomers. The stereochemistry at C-4 was assumed as R, based on spectral comparisons with (2,4-cis and trans)-bullatacinone, which has known chirality, and the fact that all 4-oxygenated acetogenins known to date are 4-R.

TABLE 1

$^1H$ NMR spectral data (δ) for 1–4.

$^1H$ NMR (500 MHz, $CDCl_3$, J in Hz)

| Position | 1 trans | 1 cis | 2 | 3 | 4 |
|---|---|---|---|---|---|
| 1 | — | — | — | — | — |
| 2 | 3.02 m | 3.03 m | — | — | — |
| 3a | 1.99 m | 1.48 m | 2.40 dddd (15.0, 8.2, 1.5, 1.5) | 2.40 dddd (15.0, 8.2, 1.5, 1.5) | 2.40 dddd (15.0, 8.2, 1.5, 1.5) |
| 4 | 4.55 dddd (8.3, 8.2, 5.7, 3.2) | 4.39 dddd (10.7, 7.4, 5.4, 5.4) | 3.87 m | 3.86 m | 3.86 |
| 5a | 1.48 m | 1.60 m | 1.48 m | 1.47 m | 1.47 m |
| 5b | 1.56 m | 1.76 m | 1.48 m | 1.47 m | 1.47 m |
| 6–7 | 1.26 br s | 1.26 br s | 1.26 br s | 1.26 br s | 1.26 br s |
| 8 | 2.40 t (7.5)[a] | 2.40 t (7.5)[a] | 2.40 t (7.5)[a] | 2.40 t (7.5)[a] | 2.40 t (7.0)[a] |
| 9 | — | — | — | — | — |
| 10 | 2.42 t (7.5)[a] | 2.42 t (7.5)[a] | 2.42 t (7.5)[a] | 2.42 t (7.5)[a] | 2.42 t (7.5)[a] |
| 11–13 | 1.26 br s | 1.26 br s | 1.26 br s | 1.26 br s | 1.26 br s |
| 14 | 1.41 m | 1.41 m | 1.41 m | 1.41 m | 1.41 m |
| 15 | 3.40 m | 3.40 m | 3.38 m[b] | 3.42 m | 3.40 m |
| 16 | 3.80 m | 3.80 m | 3.81 m[c] | 3.81 m | 3.79 m |
| 17 | 1.69 m, 1.99 m | 1.69 m, 1.99 m | 1.97 m, 1.56 m[d] | 1.94 m, 1.75 m | 1.99 m, 1.69 m |
| 18 | 1.69 m, 1.99 m | 1.69 m, 1.99 m | 1.87 m, 1.83 m[d] | 1.94 m, 1.75 m | 1.99 m, 1.69 m |
| 19 | 3.80 m | 3.80 m | 3.82 m[c] | 3.81 m | 3.79 m |
| 20 | 3.41 m | 3.41 m | 3.87 m[b] | 3.42 m | 3.40 m |
| 21 | 2.00 m | 2.00 m | 1.41 | 1.41 m | 1.41 m |
| 22 | 2.20 m | 2.20 m | 1.26 br s | 1.26 br s | 1.26 br s |
| 23 | 5.36 m | 5.36 m | 1.26 br s | 1.26 br s | 1.26 br s |
| 24 | 5.39 m | 5.39 m | 1.26 br s | 1.26 br s | 1.26 br s |
| 25 | 2.04 m | 2.04 m | 1.26 br s | 1.26 br s | 1.26 br s |
| 26–30 | 1.26 br s | 1.26 br s | 1.26 br s | 1.26 br s | 1.26 br s |
| 31 | 1.29 m | 1.29 m | 1.30 m | 1.29 m | 1.29 m |
| 32 | 0.88 t (7.0) | 0.88 t (7.0) | 0.88 t (7.0) | 0.88 t (7.0) | 0.88 t (7.0) |
| 33a | 2.67 dd (18.5, 9.0) | 2.61 dd (18.5, 9.0) | 7.19 d (1.5) | 7.19 d (1.5) | 7.19 d (1.5) |
| 33b | 3.04 dd (18.5, 3.0) | 3.11 (18.5, 3.0) | — | — | — |
| 34 | — | — | 5.06 dq (7.0, 1.5) | 5.06 dq (6.5, 1.5) | 5.06 dq (6.5, 1.5) |
| 35 | 2.20 s | 2.20 s | 1.44 d (6.5) | 1.44 d (7.0) | 1.44 d (7.0) |

[a–d]Values may be interchangeable in each column.

TABLE 2

$^{13}C$ NMR spectral data (δ) for 1–4.

$^{13}C$ NMR (125 MHz in $CDCl_3$ for 1, 3; 75 MHz in $CDCl_3$ for 2, 4)

| Position | 1 cis | 1 trans | 2 | 3 | 4 |
|---|---|---|---|---|---|
| 1 | 178.66 | 178.12 | 174.63 | 174.70 | 174.61 |
| 2 | 44.17 | 43.68 | 131.04 | 131.09 | 131.03 |
| 3 | 34.41 | 34.41 | 33.34 | 33.35 | 33.30 |
| 4 | 78.98 | 78.54 | 69.60 | 69.62 | 69.56 |
| 5 | 36.65 | 35.39 | 37.01 | 37.00 | 36.98 |
| 6 | 24.97[a] | 24.97[a] | 25.95[a] | 25.67[a] | 25.55[a] |
| 7 | 24.90–35.32 | 24.90–35.32 | 25.12–29.64 | 23.44–29.67 | 23.44–33.30 |
| 8 | 42.71[b] | 42.71[b] | 42.67[b] | 42.64[b] | 42.64[b] |
| 9 | 210.80 | 210.80 | 211.38 | 211.50 | 211.40 |
| 10 | 42.36[b] | 42.36[b] | 42.51[b] | 42.51[b] | 42.51[b] |
| 11–12 | 23.68–33.46 | 24.90–35.32 | 25.12–29.64 | 23.44–29.67 | 23.44–33.30 |
| 13 | 25.32[a] | 25.32[a] | 25.28[a] | 25.32[a] | 25.26[a] |
| 14 | 33.19[c] | 33.19[c] | 32.94[c] | 34.07[c] | 33.39[c] |
| 15 | 73.49[d] | 73.49[d] | 74.21[d] | 74.38[d] | 74.05[d] |

TABLE 2-continued

$^{13}$C NMR spectral data ($\delta$) for 1–4.

$^{13}$C NMR (125 MHz in CDCl$_3$ for 1, 3; 75 MHz in CDCl$_3$ for 2, 4)

| Position | 1 cis | 1 trans | 2 | 3 | 4 |
|---|---|---|---|---|---|
| 16 | 82.63 | 82.63 | 83.18$^c$ | 82.66 | 82.66$^c$ |
| 17 | 28.69 | 28.69 | 28.57$^f$ | 28.10 | 28.73 |
| 18 | 28.69 | 28.69 | 25.23$^f$ | 28.10 | 28.73 |
| 19 | 82.63 | 82.63 | 82.14$^c$ | 82.66 | 82.58$^c$ |
| 20 | 73.91$^d$ | 73.91$^d$ | 71.51$^d$ | 74.28$^d$ | 73.89$^d$ |
| 21 | 33.46$^e$ | 33.46$^e$ | 32.51$^e$ | 33.73$^e$ | 33.39$^e$ |
| 22 | 23.27$^a$ | 23.27$^a$ | 25.12$^a$ | 25.14$^a$ | 25.13$^a$ |
| 23 | 128.92 | 128.92 | 25.12–29.64 | 23.44–29.67 | 23.44–33.30 |
| 24 | 130.78 | 130.78 | 25.12–29.64 | 23.44-29.67 | 23.44–33.30 |
| 25 | 27.21$^a$ | 27.21$^a$ | 25.12–29.64 | 23.44–29.67 | 23.44–33.30 |
| 26–29/31 | 23.68–33.46 | 24.90–35.52 | 25.12–29.64 | 23.44–29.67 | 23.44–33.30 |
| 30/32 | 31.87 | 31.87 | 31.89 | 31.90 | 31.86 |
| 31/33 | 22.63 | 22.63 | 22.64 | 22.66 | 22.66 |
| 32/34 | 14.05 | 14.05 | 14.09 | 14.09 | 14.07 |
| 33/35 | 35.39 | 35.39 | 151.93 | 151.98 | 151.92 |
| 34/36 | 205.50 | 205.50 | 78.01 | 78.03 | 77.99 |
| 35/37 | 23.68 | 23.68 | 19.07 | 19.07 | 19.05 |

$^{a-f}$Values may be interchangeable in each column.

Resonances at $\delta$ 3.40 (H-15, H-20) and 3.80 (>-16, H-19) in the $^1$H NMR spectrum and $\delta$ 73.49 (C-15), 82.6 (C-16, 19), and 73.9 (C-20) in the $^{13}$C NMR spectrum indicated the presence of a single THF ring and two flanking hydroxyls with a threo/trans/threo relative stereochemistry. The presence of the two hydroxyls was supported by two successive losses of water from the CIMS MH$^+$ ion at m/z 621. The ring was placed between C-15 and C-20 based on EIMS peaks at m/z 325 and 395. The presence of hydroxyl groups was corroborated by a broad absorbance in the IR (3439 cm$^{-1}$) as was the existence of a carbonyl (1713 cm$^{-1}$) somewhere along the aliphatic chain. A carbonyl in the structure was also suggested by a pair of triplets in the $^1$H NMR with resonances at $\delta$ 2.40 (H-8) and 2.42 (H-10) and by a carbonyl signal at $\delta$ 210.8 (C-9) in the $^{13}$C NMR. The carbonyl position was suggested to be at C-9 based on a peak at m/z 225 in the EIMS of 1. This assignment was predicated on the assumption that cleavage was between C-9 and C-10, assuming that the oxygen was included in the fragment ion. An EIMS peak at m/z 225 would also be seen for a carbonyl at C-11 if cleavage was between C-10 and C-11. The carbonyl was placed conclusively at C-9 by the high resolution EIMS of the fragment peak at m/z 225. The m/z of 225.1131 (225.1127 calcd.) dictated that the composition of the fragment was C$_{12}$H$_{17}$O$_4$ as predicted by the above cleavage. The structure of 1 also contained a cis double bond as evidenced by $^1$H resonances at $\delta$ 5.36 and 5.39 (J=15 Hz) and $^{13}$C resonances at $\delta$ 128.9 and 130.8. This double bond was placed two methylene units away from the flanking hydroxyl based on a cross-peak in the double-relayed COSY spectrum between the methine protons at $\delta$ 5.36 (H-23) and 3.41 (H-20).

The absolute stereochemistries of the chiral centers in 1 were determined by preparing the di-(R)- and (S)-methoxy-(trifluoromethyl)-phenylacetate (MTPA) ester derivatives Kosher esters). According to advanced Mosher ester methodology, the absolute stereochemistry of a secondary alcohol is found by analyzing the difference in $^1$H NMR chemical shifts between the S- and R-MTPA ester derivatives on both sides of the carbinol center. Analysis of the $^1$H—$^1$H COSY for mosinone A-S-MTPA (1a) and mosinone A-R-MTPA (1b) suggested that, based on Mosher's arguments, the absolute stereochemistry for mosinone A was C-15R and C-20R (Table 3). Thus, the structure of 1 was elucidated and was named mosinone A.

TABLE 3

$^1$H NMR (500 MHz, CDCl$_3$) data ($\delta$) for MTPA derivatives of Compound 1.

| MTPA ester | 14 | 16 | 17 | 18 | 19 | 21 |
|---|---|---|---|---|---|---|
| 1a | 1.64, 1.60 | 3.93 | 1.64, 1.38 | 1.64, 1.38 | 3.93 | 1.60, 1.56 |
| 1b | 1.60, 1.56 | 4.01 | 1.91, 1.57 | 1.91, 1.57 | 4.01 | 1.60, 1.56 |
| $\Delta(\delta S-\delta R)$ | pos | neg | neg | neg | neg | pos |
| configuration | 15R | | | 20R | | |

Compound 2 was isolated as a white waxy solid. The CIMS showed an MH$^+$ peak at m/z 595 indicating that this compound was only 35 carbons long, unlike 1 which was two methylene units longer. The molecular composition of C$_{35}$H$_{62}$O$_7$ was confirmed by HRFABS. Signals in the $^1$H NMR of 2 at $\delta$ 7.19 (H-35), 5.06 (H-34), and 1.44 (H-33) (Table 1) implied that the structure of 2 contained an $\alpha,\beta$-unsaturated $\gamma$-lactone. $^{13}$C NMR resonances at $\delta$ 174.6 (C-1), 131.04 (C-2), 151.9 (C-33), and 78.0 (C-34) (Table 2) substantiated this hypothesis. Further evidence for the presence of an $\alpha,\beta$-unsaturated $\gamma$-lactone was provided by the IR carbonyl peak at 1755 cm$^{-1}$. The existence of hydroxyl groups in the structure was suggested by a broad absorbance in the IR (3441 cm$^{-1}$) as well as peaks in the EIMS at m/z 577, 559, and 541 indicating three successive losses of water from the molecular ion at m/z 595. Examination of the regions around $\delta$ 3.80 (H4, H15/20, H-16/19) and $\delta$ 3.40 (H-15/20) in the $^1$H spectrum of 2 and $^{13}$C NMR signals for 2 at $\delta$ 74.2 (C-15/20), 83.2 (C-16/19), 82.1 (C-16/19), and 71.5 (C-15/20) indicated a mono-THF ring acetogenin with two flanking hydroxyls. Other $^1$H signals for the ring methines (H-17/18) at $\delta$ 1.97, 1.87, 1.83, and 1.56, and $^{13}$C NMR signals at $\delta$ 32.9 and 32.5 (C-14/21) and at $\delta$ 28.6 and 25.2 (C-17/18) suggested a relative stereochemistry of threo/trans/erythro. These resonances matched those of a synthetic model compound and supported this assignment. The fragment peak in the EIMS at m/z 325 placed the THF ring between C-15 and C-20. As in 1, a carbonyl moiety along the aliphatic chain in 2 was evidenced by a second carbonyl peak in the IR (1702 cm$^{-1}$), $^1$H NMR signals at $\delta$ 2.40 (H-8) and 2.42 H-10), and a $^{13}$C NMR carbonyl signal at $\delta$ 211.4 (C-9). Similarly, the position of the carbonyl was placed at C-9 by an EIMS fragment peak at m/z 225 and verified by HREIMS spectral analysis of that fragment as described above for 1.

Although the relative stereochemistry of threo/trans/erythro could be assigned in 2 based on NMR comparisons with model compounds, it was unknown whether the erythro hydroxyl was at C-15 or C-20. Analysis of the $^1$H—$^1$H COSY spectra for the tri(S)- and tri-(R)-MTPA esters of 2 (2a and 2b, respectively) provided no information, which could stereochemically differentiate the H-16, H-17ab, H-18ab, and H-19 protons (Table 4), although the absolute stereochemistry at C-4 was conclusively determined to be R. Due to the coplanarity of the threo/trans/erythro relationship in 2, these protons experienced shielding effects of the phenyl groups of both flanking MTPA esters. Therefore, ambiguity remains concerning the relative and absolute stereochemistries of 2.

TABLE 4

$^1$H NMR (500 MHz, CDCl$_3$) data (δ) for MTPA derivatives of Compound 2.

| MTPA ester | H-5 | H-3a | H3b | H33 | H34 | H35 |
|---|---|---|---|---|---|---|
| 2a | 1.72, 1.62 | 2.61 | 2.55 | 6.73 | 4.86 | 1.28 |
| 2b | 1.61, 1.56 | 2.67 | 2.59 | 6.97 | 4.91 | 1.30 |
| Δ(δS-δR) | pos | neg | neg | neg | neg | pos |
| configuration | | | | 4R | | |

The structure of 3 differs from 2 only in the relative stereochemistry around the THF ring. The CIMS and EIMS spectra for 3 were identical to those of 2 since they have the same planar structure. As in 2, analysis of the IR, $^1$H NMR and $^{13}$C NMR spectra of 3 indicated the presence of an α,β-unsaturated γ-lactone and a single THF ring with two flanking hydroxyls. A carbonyl in the structure was again suggested by IR, $^1$H NMR (Table 1), and $^{13}$C NMR (Table 2) spectra. The assignment of the carbonyl to the C-9 position was made as before by the EIMS peak at m/z 225 and was corroborated by HREIMS of that fragment ion.

For 3, the cis assignment across the THF ring was made based on $^1$NMR signals for the rig methines at δ 1.94 and 1.75 compared to δ 1.99 and 1.69 for a trans ring configuration. $^{13}$C NMR resonances at δ 74.38, 82.66, 34.07, 33.73, and 28.10 also suggested a cis assignment for the THF ring. These signals showed a close resemblance to those of a synthetic model compound with a threo/cis/threo ring configuration, and supported this assignment. To determine the absolute stereochemistry of 3, the tri-(S)- and (R)-MTPA ester derivatives (3a and 3b, respectively) were prepared. Analysis of the $^1$H NMR and $^1$H—$^1$H COSY spectral data indicated that the absolute configuration(s) at C-4 and C-15 are R and at C-20 is S (Table 5). The structure of 3 is named mosin C.

Annoreticuin-9-one (4) has been isolated previously from *Annona reticulate*, but has not been isolated previously from *Annona squamosa*. Compound 4 was obtained as a white waxy solid and is closely related to squamone (isolated from *A. squamosa*). The only difference between compound 4 and squamone is that 4 possesses an α,β-unsaturated γ-lactone with a hydroxyl at C-4 instead of the ketolactone moiety seen in squamone. Examination of the diagnostic peaks in the $^1$H NMR (Table 1) and $^{13}$C NMR (Table 2) of 4 indicated the presence of the aforementioned lactone and hydroxyl at C-4 and a single THF ring bearing a threo/trams/threo relationship.

Although the planar structure of 4 is known, its absolute stereochemistry has not been reported previously. The tri-(R)- and (S)-Mosher esters of 4 were prepared (4a and 4b, respectively) and analyzed using $^1$H NMR and $^1$H—$^1$H COSY spectral data (Table 5). The absolute stereochemistry of 4 was determined to be 4R, 15R, 20R, and it can now be assumed that squamone has the same stereochemistry.

Compounds 1–4 all showed activity in the brine shrimp assay (Table 6). In cell culture, these acetogenins all exhibited up to 10,000 fold cytotoxic selectivities for the pancreatic cell line, PACA-2, and were 10 to 100 times more active than the positive control, adciamycin (Table 6).

TABLE 5

$^1$H NMR (500 MHz, CDCl$_3$) data (δ) for MTPA derivatives of Compounds 3 and 4.

| MTPA ester | 5 | 3 | 33 | 34 | 35 | 14 | 16 | 17 | 18 | 19 | 21 |
|---|---|---|---|---|---|---|---|---|---|---|---|
| 3a | 1.64, 1.72 | 2.56, 2.61 | 6.73 | 4.87 | 1.28 | 1.32, 1.36 | 3.86 | 1.44, 1.42 | 1.37, 1.82 | 4.10 | 1.63, 1.69 |
| 3b | 1.61, 1.67 | 2.59, 2.66 | 6.97 | 4.92 | 1.31 | 1.31, 1.35 | 3.88 | 1.46, 1.43 | 1.36, 1.81 | 4.11 | 1.65, 1.70 |
| Δ(δS-δR) config. | pos 4R | neg | neg | neg | neg | pos 15R | neg | neg | pos 20S | neg | neg |
| 4a | 1.71, 1.63 | 2.55, 2.60 | 6.73 | 4.85 | 1.28 | 1.60, 1.54 | 3.92 | 1.65, 1.36 | 1.65, 1.36 | 3.92 | 1.60, 1.54 |
| 4b | 1.70, 1.61 | 2.59, 2.68 | 6.97 | 4.91 | 1.31 | 1.55, 1.48 | 4.00 | 1.91, 1.53 | 1.91, 1.53 | 4.00 | 1.55, 1.48 |
| Δ(δS-δR) config. | pos 4R | neg | neg | neg | neg | pos 15R | neg | neg | neg 20R | neg | pos |

TABLE 6

Bioactivities of compounds 1–4.

| Comp. | BST (LC$_{50}$, µg/mL) | Cytotoxicity (ED$_{50}$, µg/mL) | | | | | |
|---|---|---|---|---|---|---|---|
| | | A-549 | MCF-7 | HT-29 | A-498 | PC-3 | PACA-2 |
| 1 | $4.39 \times 10^{-1}$ | >1 | >1 | >1 | >1 | $3.19 \times 10^{-2}$ | $2.18 \times 10^{-3}$ |
| 2 | $2.93 \times 10^{-1}$ | $9.44 \times 10^{-1}$ | >1 | >1 | >1 | $3.50 \times 10^{-1}$ | $2.51 \times 10^{-4}$ |
| 3 | $1.54 \times 10^{-1}$ | $5.96 \times 10^{-1}$ | >1 | >1 | >1 | >1 | $1.17 \times 10^{-4}$ |
| 4 | $4.09 \times 10^{-1}$ | $2.73 \times 10^{-1}$ | >1 | >1 | >1 | $9.64 \times 10^{-3}$ | $2.39 \times 10^{-4}$ |
| adriamycin | $2.57 \times 10^{-1}$ | $5.27 \times 10^{-1}$ | $1.99 \times 10^{-1}$ | $2.00 \times 10^{-2}$ | $1.02 \times 10^{-2}$ | $3.21 \times 10^{-2}$ | $1.79 \times 10^{-2}$ |

In accordance with the present invention there is provided a novel mono-THF acetogenin isolated from the bark of *Annona squamosa*. Preferred compounds are those that have a mono-THF flanked by a pair of hydroxyls and also include a carbonyl group in the aliphatic chain at the C-9 position. More particularly, the compound is in substantially pure form, and is selected from the group consisting of mosinone A, mosin B, and mosin C. These compounds exhibit antitumor and insecticidal activities and thus can be used as chemothrapeutic agents or as insecticides. In accordance with one embodiment, the compounds of the present invention are utilized to form a chemotherapeutic composition.

The present invention provides pharmaceutical formulations comprising an effective amount of an acetogenin compound selected from the group consisting of compounds 1–4 for treating a patient having a tumor. As used herein, an effective amount of the acetogenin compound is defined as the amount of the compound which, upon administration to a patient, inhibits growth of tumor cells, kills malignant cells, reduces the volume or size of the tumors or eliminates the tumor entirely in the treated patient. In particular, the presently disclosed compounds demonstrate selective toxicity for pancreatic and prostate tumor cells. Compounds 1–4 all showed selective cytotoxic activity against the human pancreatic tumor cell line, PACA-2, with potency 10 to 100 times that of adriamycin.

Murisolin, murisolin A, and 16,19-cis-murisolin, are a related series of acetogenins which differ from 2, 3, and 4 only in that they do not contain a carbonyl at the C-9 position. These compounds did not show any selectivity for PACA-2 but did exhibit strong potency against other cell lines. Furthermore, unlike the compounds described in the present application, which all displayed a similar profile of activity, the murisolin series showed different activities compared to each other. For example, 16,19-cis-murisolin was several orders of magnitude less active than the other two compounds against the A-549, HT-29, and A-498 cell lines but was 100 times more potent than them against the MCF-7 cell line. From this data, it can be suggested that the carbonyl at C-9 decreases activity in five of the six cell lines tested but magnifies the potency toward the pancreatic cell line, PACA-2. Knowing that acetogenins act by inhibiting ubiquinone linked NADH oxidases that are membrane bound, a possible explanation for the observed selectivity is that the target enzymes in PACA-2 cells have a peculiar geometry making them more susceptible to acetogenins with a carbonyl at C-9.

The substantially pure compounds in accordance with this invention can be formulated into dosage forms using pharmaceutically acceptable carriers for oral or parenteral administration to patients in need of oncolytic therapy. The effective amount to be administered to a patient is typically based on body surface area, patient weight, and patient condition. The interrelationship of dosages for animals and humans (based on milligrams per meter squared of body surface) is described by Freireich, E. J., et al., *Cancer Chemother. Rep.*, 50 (4): 219 (1966). Body surface area may be approximately determined from patient height and weight (see e.g., Scientific Tables, Geigy Pharmaceuticals, Ardley, N.Y., pages 537–538 (1970)). Preferred dose levels will also depend on the attending physicians' assessment of both the nature of the patient's particular cancerous condition and the overall physical condition of the patient. Effective anti-tumor doses of the present acetogenin compounds range from about 1 microgram per kilogram to about 200 micrograms per kilogram of patient body weight, more preferably between about 2 micrograms to about 100 micrograms per kilogram of patient body weight.

Effective doses will also vary, as recognized by those skilled in the art, dependant on route of administration, excipient usage and the possibility of co-usage with other therapeutic treatments including other anti-tumor agents, and radiation therapy.

The present pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier. In one preferred aspect of the present embodiment, the acetogenin compound is dissolved in a saline solution containing 5% of dimethyl sulfoxide and 10% Cremphor EL (Sigma Chemical Company). Additional solubilng agents such as cyclodextrins, which form specific, more soluble complexes with the present acetogenin compounds, or other solubilizing agents well-known to those familiar with the art, can be utilized as pharmaceutical excipients for delivery of the acetogenin compounds. Alternatively, the present compounds can be chemically modified to enhance water solubility.

The present compound can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active acetogenins and solid carriers, and lubricants well-known to those familiar with the art. Examples of solid carriers include starch, sugar, bentonite. The compounds of the present invention can also be administered in a form of a hard shell tablet or capsule containing, for example, lactose or mannitol as a binder and a conventional fillers and tableting agents.

In accordance with one embodiment, a pharmaceutically acceptable chemotherapeutic composition is provided comprising an anti-tumor effective amount of a compound selected from the group consisting of mosinone A, mosin B, mosin C and annoreticuin-9-one, and derivatives of such compounds, and a pharmaceutically acceptable carrier therefor. These compositions can further comprise conventional fillers and solubilizing agents or other known chemotherapeutic agents.

The acetogenin compounds of the present invention can be used to treat patients having tumors. The method comprises administering to the patient an effective amount of a compound selected from the group consisting of mosinone A, mosin B, mosin C and annoreticuin-9-one. In one embodiment, a pharmaceutical composition comprising an acetogenin selected from the group consisting of mosinone A, mosin B, mosin C and annoreticuin-9-one is used to treat a patient having pancreatic or prostate cancer. In one embodiment, a pharmaceutical composition comprising an acetogenin selected from the group consisting of mosin B, mosin C and annoreticuin-9-one is used to treat a patient having pancreatic cancer, and in another embodiment a pharmaceutical composition comprising an acetogenin selected from the group consisting of mosinone A and annoreticuin-9-one is used to treat a patient having prostate cancer.

EXAMPLE 1

Isolation of the Acetogenins

General Experimental Procedures. UV spectra were measured on a Beckman DU 640 series spectrophotometer. IR data were collected using a Perkin-Elmer 1600 series ftir. $^1$H NMR and $^{13}$C NMR were obtained on a Varian VXR-500S spectrometer. Low-resolution EIMS and CIMS data were collected on a Finnigan 4000 spectrometer. High-resolution EIMS, CIMS and FABMS were obtained on the Kratos MS50 through peak matching. HPLC was carried out using a Dynamax UV-1 detector coupled with a Rainin model HPXL solvent delivery system for normal phase and Dynamax model SDS200 solvent delivery system for reversed-phase.

Plant Material. The dried stem bark of *Annona squamosa* Rich was purchased from United Chemical and Allied Products in Calcutta, India.

Extraction and Isolation. The dried and pulverized bark of (7.4 kg) was extracted with ethanol (1.83 kg F001, BST $LC_{50}$=1.5532). The residue was partitioned between $CH_2Cl_2$ and $H_2O$ to yield a dichloromethane soluble residue (842 g F003, BST $LC_{50}$=1.6774) and a water soluble residue (128.6 g F002, BST $LC_{50}$=950.1438). F003 was further partitioned between 90% aqueous methanol and hexane resulting in a methanol soluble residue (545.5 g F005, BST $LC_{50}$=1.5155) and a hexane soluble residue (162.9 g F006, BST $LC_{50}$= 122.9733). 500.5 g of F005 was separated by column chromatography over Si gel using hexane and chloroform then chloroform and methanol as solvent systems. Fractions 30–36 were combined on the basis of TLC and were fi resolved on another Si gel column eluted with hexane and acetone. The pools from this column bioactive in the BST were subjected to a third Si gel column eluted with chloroform and methanol. Compounds 1–4 were purified by repeated normal-phase and reversed-phase HPLC using solvent systems of acetonitrile water and hexane:methanol:THF, respectively.

Derivatizations. To 14 (0.5 mg in 0.5 mL $CH_2Cl_2$) were sequentially added 0.2 mL pyridine, 0.5 mg 4-(dimethylamino)-pyridine, and 12 mg of (R)-(-)-(α-methoxy-α-trifluoromethyl)-phenylacetyl chloride or (S)-(+)-α-methoxy-α-(trifluoromethyl)-phenylacetyl chloride. The mixture was stirred for 4 h at room temperature then passed through a small pipet column (0.6×6 cm) packed with Si gel and eluted with 5 mL $CH_2Cl_2$. The residue was redissolved in 5 mL $CH_2Cl_2$ and washed with 5 mL 1% $NaHCO_3$ and 2×5 mL $H_2O$. The organic layer was evaporated to give the S-Mosher esters of 1–4. Use of (5)(+)-α-methoxy-α-(trifluoromethyl)-phenylacetyl chloride yielded the R-Mosher esters of 1–4.

Mosinone A (1).—White waxy solid (12 mg); $[\alpha a]^{23}{}_D$=+4.8°0; (c=0.016, $CH_2Cl_2$) UV (MeOH) $\lambda_{max}$202 nm (log ε=2-96); CIMS (isobutane) m/z {MH}$^+$ 621 (64), {MH-$H_2O$}$^+$ 603 (100), {MH-2$H_2O$)$^+$ 585); EIMS m/z 395(5), 377(20), 359(19), 325(100), 307(40), 289(13), 225(16), 207 (20); HRCIMS (isobutane) m/z 621.4723 for $C_{37}H_{60}O_7$ (calcd. 621.4730); HREIMS m/z 225.1131 for $C_{12}H_{17}O_4$ (calcd. 225.1127); $^1$H NMR data (CDCl$_3$, 500 MHz), see Table 1; $^{13}$C NMR (CDCl$_3$, 125 MHz), see Table 2.

Mosin B (2).—White waxy solid (7 mg); $[\alpha]^{23}{}_D$=+11.5° (c=0.005, $CH_2Cl_2$); UV (MeOH)$\lambda_{max}$=222 nm (log ε=3.57); CIMS (isobutane) m/z 595(30), 577(71), 559(37); EIMS m/z 325(16), 307(91), 289(62), 225(7), 207(69); HRFABMS m/z 595.4578 for $C_{35}H_{62}O_7$ (calcd. 595.4574); HREIMS 225.1133 for $C_{12}H_{17}O_4$ (calcd. 225.1127); $^1$H NMR data (CDCl$_3$, 500 MHz), see Table 1; $^{13}$C NMR data (CDCl$_3$, 75 MHz), see Table 2.

Mosin C (3).—White waxy solid (6 mg);$[\alpha]^{23}{}_D$=-2.7° (c=0.007, $CH_2Cl_2$); UV (MeOH) $\lambda_{max}$=216 nm (log ε=3.56); CIMS (isobutane) m/z 595(74), 577(100), 559(53); EIMS m/z 325(16), 307(14), 289(9), 225(4), 207(10); HRFABMS m/z 595.4578 for $C_{35}H_{62}O_7$ (calcd. 595.4574); HREIMS 225.1135 for $C_{12}H_{17}O_4$ (calcd. 225.1127); $^1$H NMR data (CDCl$_3$, 500 MHz), see Table 1; $^{13}$C NMR data (CDCl$_3$, 125 MHz), see Table 2.

EXAMPLE 2

Bioassays

The brine shrimp (*Artemia salina* Leach) test (BST) was performed, as described in Meyer et al. *Planta Med.* 45, p. 31–34 (1982), to determine $LC_{50}$ values in μ/ml. Seven-day in vitro cytotoxicity tests against human tumor cell lines were carried out at the Purdue Cancer Center, using standard protocols for A-549 (human lung carcinoma), MCF-7 human breast carcinoma), HT-29 (human colon carcinoma), A498 (human kidney carcinoma), PC-3 (human prostate carcinoma), and PACA-2 (human pancreatic carcinoma) with adriamycin as a positive control.

Compounds 14 all showed activity in the brine shrimp assay. In cell culture, these acetogenins all exhibited up to 10,000 fold cytotoxic selectivities for the pancreatic cell line, PACA-2, and were 10 to 100 times more active than the positive control adriamycin (Table 6).

What is claimed is:

1. A substantially pure form of a compound selected from the group consisting of mosinone A, mosin B, and mosin C.

2. A composition comprising an anti-tumor effective amount of a compound selected from the group consisting of mosinone A, mosin B, and mosin C and a pharmaceutically acceptable carrier therefor.

3. A method for treating a patient having a tumor, said method comprising the step of administering to the patient an effective amount of a compound selected from the group consisting of mosinone A, mosin B, mosin C and annoreticuin-9-one.

4. The method of claim 3 wherein the patient to be treated has pancreatic or prostate cancer.

* * * * *

UNITED STATES PATENT AND TRADEMARK OFFICE
CERTIFICATE OF CORRECTION

PATENT NO. : 6,242,483 B1
DATED : June 5, 2001
INVENTOR(S) : McLaughlin et al.

It is certified that error appears in the above-identified patent and that said Letters Patent is hereby corrected as shown below:

Column 12,
Line 56, should read:
-- 3. A method of treating a patient having a tumor, said method comprising the step of administering to the patient an effective amount of a compound selected from the group consisting of mosinone A, mosin B, <u>and</u> mosin C [and annoreticuin-9-one]. --

Signed and Sealed this

Twenty-fifth Day of June, 2002

Attest:

Attesting Officer

JAMES E. ROGAN
*Director of the United States Patent and Trademark Office*